(12) United States Patent
Labbe

(10) Patent No.: US 11,517,475 B2
(45) Date of Patent: Dec. 6, 2022

(54) DUAL HELICAL COIL OPHTHALMIC SURGICAL INSTRUMENTS FOR REMOVAL OF LENS MATERIALS AND METHODS OF USE

(71) Applicant: Thad Anthony Labbe, Georgetown, TX (US)

(72) Inventor: Thad Anthony Labbe, Georgetown, TX (US)

( * ) Notice: Subject to any disclaimer, the term of this patent is extended or adjusted under 35 U.S.C. 154(b) by 79 days.

(21) Appl. No.: 17/083,268

(22) Filed: Oct. 28, 2020

(65) Prior Publication Data

US 2021/0038430 A1 Feb. 11, 2021

Related U.S. Application Data

(63) Continuation of application No. 16/701,080, filed on Dec. 2, 2019, now abandoned, which is a continuation-in-part of application No. 16/112,693, filed on Aug. 25, 2018, now abandoned.

(51) Int. Cl.
| | | |
|---|---|---|
| *A61F 9/007* | (2006.01) | |
| *A61B 17/285* | (2006.01) | |
| *A61B 17/00* | (2006.01) | |
| *A61B 17/28* | (2006.01) | |

(52) U.S. Cl.
CPC ........ *A61F 9/00754* (2013.01); *A61B 17/282* (2013.01); *A61B 17/285* (2013.01); *A61B 17/2841* (2013.01); *A61B 2017/00398* (2013.01); *A61B 2017/2845* (2013.01)

(58) Field of Classification Search
CPC ....... A61F 9/00754; A61B 2017/00398; A61B 17/282; A61B 17/2841; A61B 2017/2845; A61B 17/285
See application file for complete search history.

(56) References Cited

U.S. PATENT DOCUMENTS

| | | | |
|---|---|---|---|
| 3,683,891 A | * | 8/1972 | Eskridge ................ A61B 10/04 30/113.1 |
| 3,976,077 A | | 8/1976 | Kerfoot, Jr. |
| 4,000,745 A | | 1/1977 | Goldberg |
| 4,653,496 A | | 3/1987 | Bundy |
| 4,745,919 A | * | 5/1988 | Bundy ............... A61B 17/3207 604/164.11 |
| 5,135,530 A | | 8/1992 | Lehmer |
| 5,156,607 A | | 10/1992 | Kansas |
| 5,451,230 A | | 9/1995 | Steinert |
| 6,719,805 B1 | | 4/2004 | Ahern |

(Continued)

*Primary Examiner* — Jing Rui Ou
(74) *Attorney, Agent, or Firm* — Hulsey P.C.

(57) ABSTRACT

An ophthalmic surgical instrument for cataract removal surgery includes a helical coil structure including a wire or elongated structure coiled in a plurality essentially similar diameter coils of 360-degree turns in a corkscrew having a coil diameter sufficiently small to fit within an incision of a human ocular lens capsule for entering the human ocular lens capsule during a cataract removal surgery. A pointed sharp end pierces and grasps a human ocular lens under the control of a surgeon upon being inserted in a human ocular lens capsule within said ocular lens capsule during a cataract removal surgery. The corkscrew structure firmly holds the human ocular lens and controls the position and movement of the human ocular lens during said cataract removal surgery.

4 Claims, 10 Drawing Sheets

(56) References Cited

U.S. PATENT DOCUMENTS

| | | | |
|---|---|---|---|
| 6,911,019 B2 * | 6/2005 | Mulier | A61B 18/1477 |
| | | | 606/41 |
| 9,220,892 B2 * | 12/2015 | Faure | A61B 18/1482 |
| 9,993,231 B2 * | 6/2018 | Costello | A61B 10/0266 |
| 10,667,855 B1 * | 6/2020 | To | A61B 90/11 |
| 2001/0031951 A1 | 10/2001 | Pezzola | |
| 2002/0026176 A1 | 2/2002 | Varner | |
| 2002/0091351 A1 | 7/2002 | Rockley | |
| 2002/0095113 A1 | 7/2002 | Kishimoto | |
| 2002/0111608 A1 | 8/2002 | Baerveldt | |
| 2002/0165522 A1 | 11/2002 | Holmen | |
| 2003/0004455 A1 | 1/2003 | Kadziauskas | |
| 2003/0050629 A1 | 3/2003 | Kadziauskas | |
| 2003/0055442 A1 | 3/2003 | Laufer | |
| 2003/0135226 A1 | 7/2003 | Bolduc | |
| 2003/0158567 A1 | 8/2003 | Ben-Nun | |
| 2004/0254520 A1 | 12/2004 | Porteous | |
| 2006/0020326 A9 | 1/2006 | Bolduc | |
| 2008/0140203 A1 | 6/2008 | Davis | |
| 2010/0152626 A1 | 6/2010 | Schwartz | |
| 2011/0264130 A1 | 10/2011 | Glazer | |
| 2015/0320597 A1 | 11/2015 | Jacobovitz | |
| 2017/0007452 A1 | 1/2017 | Depenbusch | |

* cited by examiner

DUAL HELICAL COIL OPHTHALMIC SURGICAL INSTRUMENTS FOR REMOVAL OF LENS MATERIALS AND METHODS OF USE

RELATED APPLICATIONS

This is a continuation application and claims the benefit of U.S. Non-Provisional application Ser. No. 16/112,693, titled "A CATARACT GRASPING DEVICE FOR ASSISTING IN CATARACT REMOVAL SURGERY" filed on Aug. 25, 2018, and U.S. Non-Provisional application Ser. No. 16/701,080, titled "OPHTHALMIC SURGICAL INSTRUMENTS FOR REMOVAL OF LENS MATERIALS AND METHODS OF USE" filed on Dec. 2, 2019. All documents and references cited herein, and in the above referenced application, are hereby expressly incorporated by reference in their entirety.

FIELD OF THE INVENTION

The present disclosure relates to ophthalmic surgical instruments and instruments for surgery of the eye and, more specifically, to ophthalmic surgical instruments designed to be used upon the eye for removing eye lens materials. Yet more specifically, the subject matter of the present disclosure relates to methods and instruments designed to remove portions of the eye to effect removing eye lens material during cataract surgery.

BACKGROUND OF THE INVENTION

The eye is a very fragile organ, and requires extreme care before, during, and after a surgical procedure to minimize or prevent further damage. An expert eye surgeon is responsible for selecting the appropriate surgical procedure for the patient, and for taking the necessary safety precautions. Today, eye surgery continues to be a widely practiced type of surgery, having developed various techniques for treating eye problems A cataract is an opacification or cloudiness of the eye's crystalline lens due to aging, disease, or trauma that typically prevents light from forming a clear image on the retina. Cataract increases the opacity of the lenses of the eyes. The result is gradual and progressive impairment of vision. If left untreated, cataract can cause loss of vision. If visual loss is significant, surgical removal of the lens may be warranted, with lost optical power usually replaced with a plastic intraocular lens.

Common symptoms include seeing halos around lights, cloudy or blurred vision with sensitivity to glare and light. In cataract surgery, the affected lens is removed and replaced with an artificial one, called an intraocular lens. Owing to the high prevalence of cataracts, cataract extraction is the most common eye surgery. Cataract surgeries vary in types, depending on the patient's condition and preferences. For each type, additional cataract surgery instruments are used to suit the needs of the surgeon.

Cataract surgery requires a standard set of cataract surgical instruments due to the delicate nature of the eyes. General instruments may be too large and coarse for use in this surgical procedure, which may do more damage than good. Examples of cataract surgical instruments include a Castroviejo caliper to measure size of the incision. Colibri forceps are fine and smooth forceps have special 0.12 1×2 teeth used for holding cornea. Capsulorhexis forceps are fine sharp-tipped forceps are used to make a continuous curvilinear incision on the anterior capsule of the lens. Capsulotomy forceps create an incision in the anterior capsule of the lens during cataract surgery.

Nucleus removing forceps are useful to force out the lens in extracapsular type of cataract extraction. Designed to remove fragments of the nucleus through a small incision, it has two rows of delicate teeth on jaws. A diamond knife is an angled phaco micro-surgical knife used in making sclerocorneal tunnels in small incision type of cataract surgery.

Surgical methods used to remove cataracts may also include using an ultrasound probe to break up the lens for removal. During a procedure called phacoemulsification (fak-o-e-mul-sih-fih-KAY-shun), a surgeon makes a tiny incision in the front of the eye (cornea) and inserts a needle-thin probe into the lens substance where the cataract has formed. The surgeon then uses the probe, which transmits ultrasound waves, to break up (emulsify) the cataract and suction out the fragments. The very back of the lens (the lens capsule) is left intact to serve as a place for the artificial lens to rest. Stitches may or may not be used to close the tiny incision in the cornea at the completion of the procedure.

Complications after cataract surgery are uncommon, and most can be treated successfully. Cataract surgery risks include inflammation, infection, bleeding, swelling, dislocation of artificial lens, retinal detachment, loss of vision. Though uncommon, these complications can be painful and detrimental to the patient. So, continuing improvements are needed in cataract surgical instruments to continue to reduce and eliminate these complications during and following cataract surgery.

There are three different types of cataracts. A sub-capsular cataract occurs at the back of the lens. People with diabetes or those taking high doses of steroid medications have a greater risk of developing a sub-capsular cataract. A nuclear cataract forms deep in the central zone (nucleus) of the lens. Nuclear cataracts usually are associated with aging. A cortical cataract is characterized by white, wedge-like opacities that start in the periphery of the lens and work their way to the center in a spoke-like fashion. This type of cataract occurs in the lens cortex, which is the part of the lens that surrounds the central nucleus.

FIGS. 1A and 1B present a human eye 10 before (FIG. 1A) and after (FIG. 1B) a cataract removal surgery. Cataract surgery is a procedure to remove lens 12 of the eye and, in most cases, replace it with an artificial lens. Normally, lens 12 of the eye is clear. A cataract causes lens 12 to become cloudy, which eventually affects the vision.

FIGS. 2A and 2B illustrate a cut-away view of a human eye 10 during cataract surgery. FIG. 2A shows ultrasound probe 18 penetrating lens capsule 20 for treating cataract 12. Cataract 12 appears below iris 22. Ultrasound probe 18 breaks apart or cuts cataract 12. The surgeon must be careful not to penetrate beyond the back portion of lens 24. Otherwise, lens capsule 20 damage may occur. FIG. 2B shows that once the cataract 16 has been separated, using a removal instrument 26, the surgeon seeks to grasp cataract 16 for its removal from lens capsule 20.

FIGS. 2A and 2B, thus, indicate one surgery type for removing a cataract which may benefit from the device and method of the present disclosure. Cataract surgery is performed by an eye doctor (ophthalmologist) on an outpatient basis, which means the patient generally does not need to stay in the hospital after the surgery. Cataract surgery can be done traditionally using ultrasound energy to remove the cloudy lens or it can be removed with laser-assisted technology. Cataract surgery is very common and is generally a safe procedure.

Nearly everyone who has cataract surgery will be given an artificial lens called an intraocular lens (IOL). These lenses improve vision by focusing light on the back of the eye. The patient does not see or feel the lens, which requires no care and becomes a permanent part of the eye. IOLs are made of plastic, acrylic or silicone. Some IOLs block ultraviolet light. Some IOLs are rigid plastic and implanted through an incision that requires several stitches (sutures) to close. Once the cataract has been removed by either phacoemulsification or extracapsular extraction, the artificial lens is implanted into the empty lens capsule.

After cataract surgery, the vision generally begins improving within a few days. The vision may be blurry at first as the eye heals and adjusts. Colors may seem brighter after the surgery because the patient is looking through a new, clear lens. A cataract is usually yellow- or brown-tinted before surgery, muting the look of colors.

From a surgeon's perspective there may be instances of particularly difficult cases. For example, if the patient had a very dense cataract, a problem may arise in association with the removal of a cataract. In this situation, an instrument enables the surgeon to break up the cataract through the use of suction. When this and similar methods are used, cataract pieces arising from breaking up of the cataract must be removed from the lens capsule. The problem with dense cataract removal is that the very dense cataract resists being grasped with a suction provided by the open bored phacoemulsification instrument. The lens also resists being broken into smaller pieces by the phacoemulsification energy.

In the cutting (i.e., chopping) procedure, the physician grabs the cataract and breaks the cataract. When the cataract is dense, the physician surgeon may use a very sharp instrument. This requires pulling up on the cataract during the operation. This further involves pulling on the cataract so that it can be held in position for cutting and then pushing down on it with the cutting blade so that the cutting blade may cut the cataract.

With a dense cataract, it is difficult to use the removal instrument to grasp the cataract and remove the cataract from the lens capsule. This occurs simply because it is often not possible to grasp the lens in the exceedingly fragile and sensitive lens capsule of the human eye. With small lens pieces and/or a dense or hard cataract the inability to grasp the piece or pieces can result in prolonged surgery, unnecessary stress on the lens capsule and surrounding tissue, and even damage to the eye from needing to use the hard metal surgical instruments in the delicate lens capsule region.

If the surgeon could more controllably grasp the lens at all stages of the cataract removal surgery less stress and damage from the surgery would result, smaller lens capsule incisions, and improvement in other surgical steps would occur. With fewer surgical complications and reduced incisions, recovery from cataract removal surgery will be materially and beneficially enhanced.

BRIEF SUMMARY OF THE DISCLOSURE

The disclosed subject matter provides an ophthalmic surgical instrument for assisting in cataract removal surgery, additionally the present disclosure provides an apparatus, method and system for using an ophthalmic surgical instrument for grasping a cataract during a cataract removal surgery.

The present disclosure includes a highly controllable helical coil structure including a wire or elongated structure coiled in a plurality of turns of essentially similar diameter coils of 360-degree turns. The helical coil structure has a coil diameter sufficiently small to fit within an incision of a human ocular lens capsule for entering the human ocular lens capsule during a cataract removal surgery. A pointed sharp end of the helical coil structure for piercing and grasping a human ocular lens within the ocular lens capsule during a cataract removal surgery for controlling the position and movement of the human ocular lens. An ophthalmic surgical instrument controls the position and movement of the helical coil structure during a cataract removal surgery and while the pointed sharp end engages the cataract.

The controllable helical coil structure handling mechanism is capable of rotating the helical coil structure during the cataract surgery for causing the pointed sharp end to precisely pierce the cataract progressively and controllably for more or less deeply engaging the human ocular lens during the cataract removal surgery according to the needs of the surgeon performing the cataract removal surgery.

The ophthalmic surgical instrument of the present disclosure includes a precisely controllable helical coil structure having a pitch distance of less than approximately one millimeter for permitting rotation of the ophthalmic surgical instrument for progressively and firmly engaging the human ocular lens without damaging tissue on the side of the human ocular lens opposite the side wherein the pointed sharp end pierces the human ocular lens. The ophthalmic surgical instrument includes a pointed sharp end of the helical coil structure for grasping the human ocular lens without producing heat during the cataract removal surgery for avoiding corneal endothelium heat damage during a cataract removal surgery. The ophthalmic surgical instrument further may also include a connection with a phacoemulsification device for performing phacoemulsification of the cataract to break the cataract into smaller pieces, thereby facilitating removal of a cataract from a human ocular lens capsule.

In addition, the ophthalmic surgical instrument of present disclosure further includes a viscoelastic medium for placing into the ocular anterior chamber for stabilizing the ophthalmic surgical instrument during a cataract removal surgery for safely inserting said ophthalmic surgical instrument into the eye through a small incision in the ocular lens capsule formed by a keratome or blade-like sharp device.

In one embodiment, the ophthalmic surgical instrument includes a pair of a controllable helical coil structures arranged on a hand-held scissors-like handle. The scissor-like handle permits controlled and coordinated use of the two helical coil structures to first grasp the cataract and then to split the cataract into two pieces.

This Brief Summary of the Disclosure is not intended to define the claims nor is it intended to limit the scope of the invention in any manner. Other features and advantages of the invention will be apparent from the following Drawings, Detailed Description, and the Claims.

BRIEF DESCRIPTION OF THE DRAWINGS

The present subject matter will now be described in detail with reference to the drawings, which are provided as illustrative examples of the subject matter so as to enable those skilled in the art to practice the subject matter. Notably, the figures and examples are not meant to limit the scope of the present subject matter to a single embodiment, but other embodiments are possible by way of interchange of some or all of the described or illustrated elements and, further, wherein.

DETAILED DESCRIPTION OF ILLUSTRATIVE EMBODIMENTS

Figure 1A:
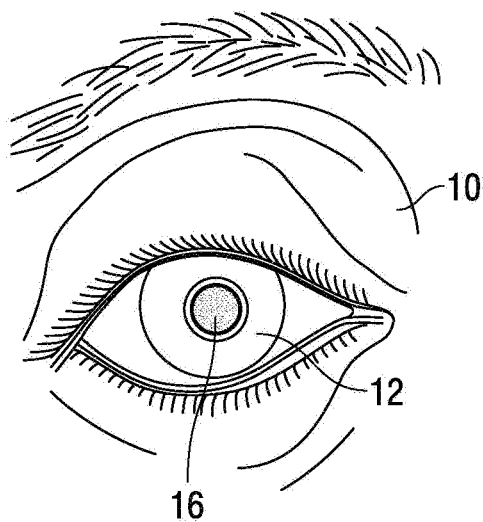
FIGS. 1A and 1B present a human eye before and after a cataract removal surgery.
Figure 1B:
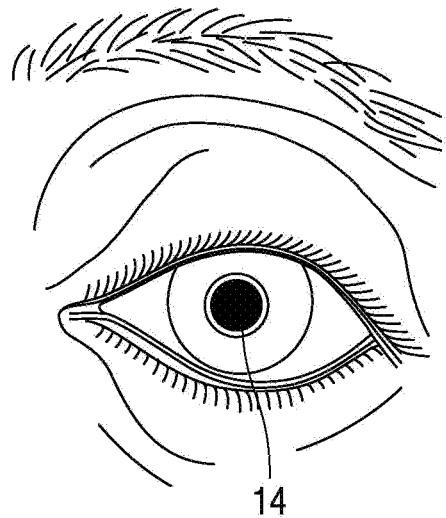
Figure 2A:
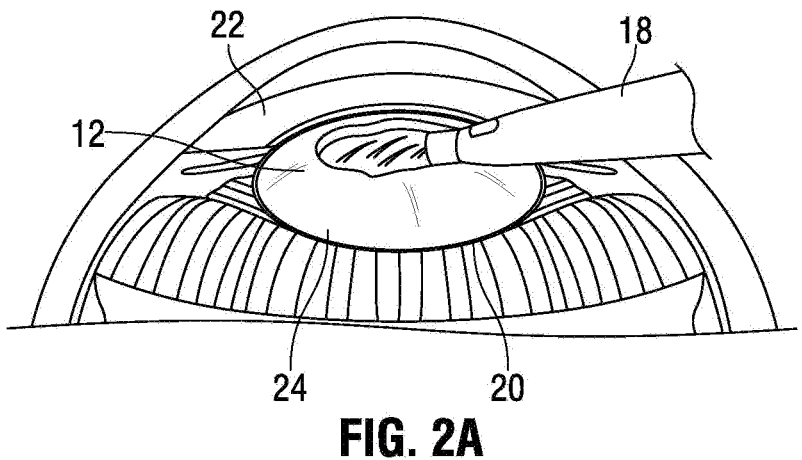
FIGS. 2A and 2B indicate one surgery type for removing a cataract which may benefit from the device and method of the present disclosure.
Figure 2B:
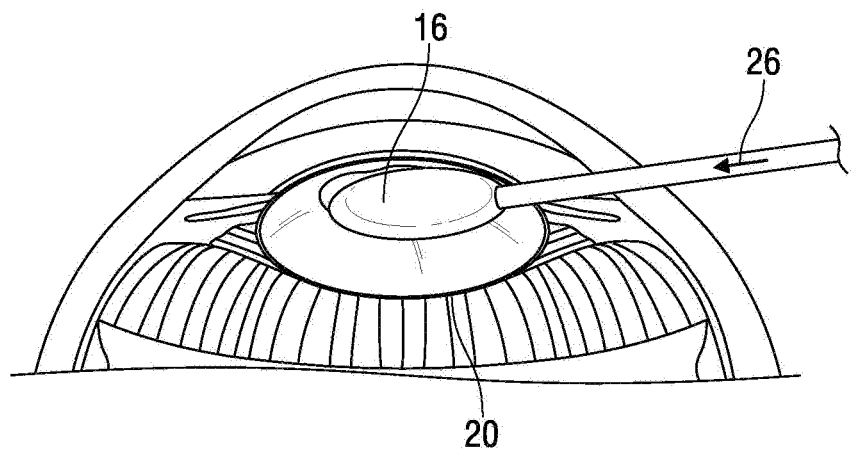

The detailed description set forth below in connection with the appended drawings is intended as a description of exemplary embodiments in which the presently disclosed process can be practiced. The term "exemplary" used throughout this description means "serving as an example, instance, or illustration," and should not necessarily be construed as preferred or advantageous over other embodiments. For the purposes of the ophthalmic surgical instruments disclosed herein, the terminology "corresponds to" means there is a functional and/or mechanical relationship between objects which correspond to each other.

The detailed description includes specific details for providing a thorough understanding of the presently disclosed method and system. However, it will be apparent to those skilled in the art that the presently disclosed process may be practiced without these specific details. In some instances, well-known structures and devices are shown in block diagram form in order to avoid obscuring the concepts of the presently disclosed method and system. Unless otherwise defined, all technical terms used herein have the same meaning as commonly understood by one of ordinary skill in the art to which this technology belongs.

In the following description, numerous details are set forth to provide an understanding of the disclosed embodiments. However, it will be understood by those of ordinary skill in the art that the disclosed embodiments may be practiced without these details and that numerous variations or modifications may be possible without departing from the scope of the disclosure.

In the present specification, an embodiment showing a singular component should not be considered limiting. Rather, the subject matter preferably encompasses other embodiments including a plurality of the same component, and vice-versa, unless explicitly stated otherwise herein. Moreover, the applicant does not intend for any term in the specification or claims to be ascribed an uncommon or special meaning unless explicitly set forth as such. Further, the present subject matter encompasses present and future known equivalents to the known components referred to herein by way of illustration.

Extra capsular cataract surgery is the most prevalent form of cataract surgery performed today. In the extracapsular technique, the clear capsule that surrounds the lens is first opened, then a loop was placed under the cataract and the cataract was slid out of the capsule. The drawback of known cataract surgeries is the large incision needed to be made reach, grasp, and remove the cataract. This process unnecessarily increases the risk of complications.

Current cataract surgery uses a small device called a phacoemulsifier that is inserted through a small incision to grasp the cataract with suction. The cataract is broken into small pieces with the phacoemulsifier. The tip of the phacoemulsifier vibrates at approximately 40,000 times per second and second part of the tip sucks the cataract. This device can be used to grasp the cataract while a second instrument is used to break the cataract into small pieces.

Figure 3:
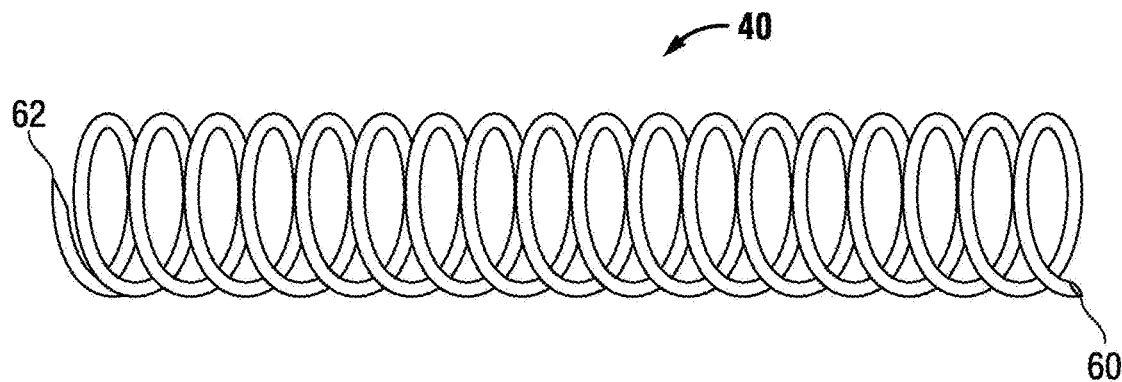
FIG. 3 displays one embodiment of the ophthalmological surgery device of the present disclosure.
Figure 4:
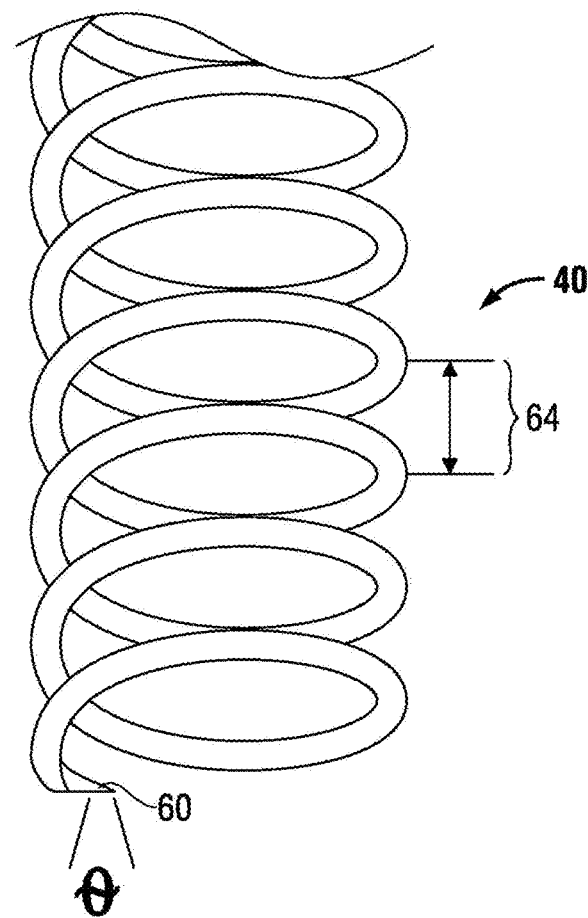
FIG. 4 portrays in more detail the characteristics of the ophthalmological surgery helical coil surgical instrument 40 of the present disclosure.

FIGS. 3 and 4 illustrate specific aspects of ophthalmic surgical instrument 40 according to the present disclosure. In particular, FIG. 3 shows that ophthalmic surgical instrument 40 may be formed of a surgical stainless-steel material. Such a material would prevent rusting and other material defects to assure that surgical instrument 40 operates for repeated procedures in the high risk surgical biocontamination environment of cataract surgery. FIG. 3, for example, shows that at one end of ophthalmic surgical instrument 40 appears the impaling end 60. Impaling end 60 has a wedge shaped and sharp point to permit easily impaling cataract 16 and lens 12.

Ophthalmic surgical instrument 40 may have various lengths. These lengths may, for example, range from approximately ½ inch to as long as 1 inch or more, depending on the material used and the particular needs of the surgeon.

FIG. 4 shows a close-up view of an end of ophthalmic surgical instrument 60 to illustrate possible dimensions of helical coil pitch 64 and cutting edge 60. Thus, in one embodiment the height of a helical coil pitch 64 may be, for example, 1 mm. Moreover, the cutting edge 60 may be of a slant theta (θ) that best supports impaling lens 12 for the removal of cataract 16.

FIG. 3 displays one embodiment of the ophthalmological surgery device of the present disclosure. A large cataract surgical incision may be approximately 7 to 8 mm. Using the ophthalmic surgical instrument of the present disclosure, it is possible to reduce the size of the capsular bag incision to 1-3 mm and perhaps even smaller. With care it may be possible to insert only ophthalmic surgical instrument 20 to penetrate the capsular bag 20 opening and not require entry of the entire helical surgical instrument 40.

A human lens is typically 3.5-5.5 mm in thickness. In the event that helical surgical surgical instrument 40 pitch is 1 mm, each full of 360° rotation of the ophthalmic surgical instrument 40 causes the cutting-edge to penetrate into the lens a full 1 mm in depth. Thus, if the helical surgical instrument is rotated 2½ turns, a depth of 2.5 mm results. At this depth, the surgeon can be certain that the cutting-edge of the helical surgical instrument will not go beyond the back side of the lens and, thus, prevent cutting damage to the capsular bag.

FIG. 4 portrays in more detail the characteristics of the ophthalmological surgery helical coil surgical instrument 40 of the present disclosure. Each additional turn of the helical surgical instrument 40 provides the surgeon with additional grasping power. Once the lens is firmly grasped with the helical surgical instrument 40, the surgeon may use another instrument 34 for the purpose of cutting the cataract lens. Using a procedure, such as vertical chop surgery, the surgeon can press down on cataract 16 with a sharp instrument while pulling up up on ophthalmic surgical instrument 40 which is firmly grasping the cataract. Ophthalmic surgical instrument 40 may, therefore, improve surgery that uses of the vertical chop procedure. This, too, will reduce resulting pressure on the capsular bag 20 and thereby avoid damage to the eye during surgery.

Another surgical option includes grasping the cataract lens 12 using ophthalmic surgical instrument 40 and then cutting cataract 16 pieces for extracting the cut pieces from capsular bag 20. Ophthalmic surgical instrument 20 permits completely controlled extraction of the cataract pieces directly from the capsular bag upon their being impaled.

Ophthalmic surgical instrument 40 of the present disclosure includes a wedge-shaped point or cutting edge that enters into the lens 12 and provides a precise instrument that impales the lens 12 in a more controllable way that also permits smaller incisions into the lens capsule 20. The sharp end of the single helix can impale and hold firmly cataract 16. By making an incision into the capsular bag 20, the surgeon has the ability to engage and grasp cataract 16 for the surgery's duration. This is a solid and firm engagement with cataract 16 that permits other instruments to be inserted for breaking down cataract 16 or otherwise for moving the cataract lens 12 in a more controlled surgery.

Ophthalmic surgical instrument 40 of the present disclosure has been demonstrated successfully in the removal of cataracts of porcine eyes. This is been shown in a closed laboratory environment for the purposes of experimental demonstration of the process the ophthalmic surgical instrument makes possible. When used in a laboratory environment for removal of cataract and pig eyes, ophthalmic surgical instrument demonstrated the ability to grasp and extract the cataract lens from the capsular bag. In addition, the ophthalmic surgical instrument showed the ability to grasp the cataract for piecewise removal, as necessary.

Ophthalmic surgical instrument 40 of the present disclosure may be included in a surgical protocol for the purpose of human eye cataract removal. Thus, the ophthalmic surgical instrument of the present disclosure may be used in combination with the device for cutting or breaking up the cataract.

Another potential use of helical surgical instrument 40 is for the capsulorhexis. When a surgeon begins the cataract surgery, he opens capsule 20 via a surgical incision. With ophthalmic surgical instrument 40 of the present disclosure, it is possible to make a single pinpoint insertion for cutting into the lens and potentially eliminating the capsulorhexis incision. Thus, ophthalmic surgical instrument 40 would simply impale or penetrate capsule 20 and by turning into capsule 20 provide for impaling and grasping cataract 16. This can be particularly advantageous if there is very swollen cataract 16 and cutting lens capsule 20 may be significantly complicated or risky.

For patients with advanced or swollen cataracts, the ability to enter lens capsule 20 for performing cataract surgery can be restricted or limited. By virtue of using the a above disclosed capsulorhexis step, the swollen or enlarged cataract, and be relieved of pressure and/or be more delicately handled to minimize injury or heat. Using the presently disclosed ophthalmic surgical instrument, the swollen or pressurize fluid may be removed controllably to permit further progress and controlled operation of the cataract removal.

Figure 5:
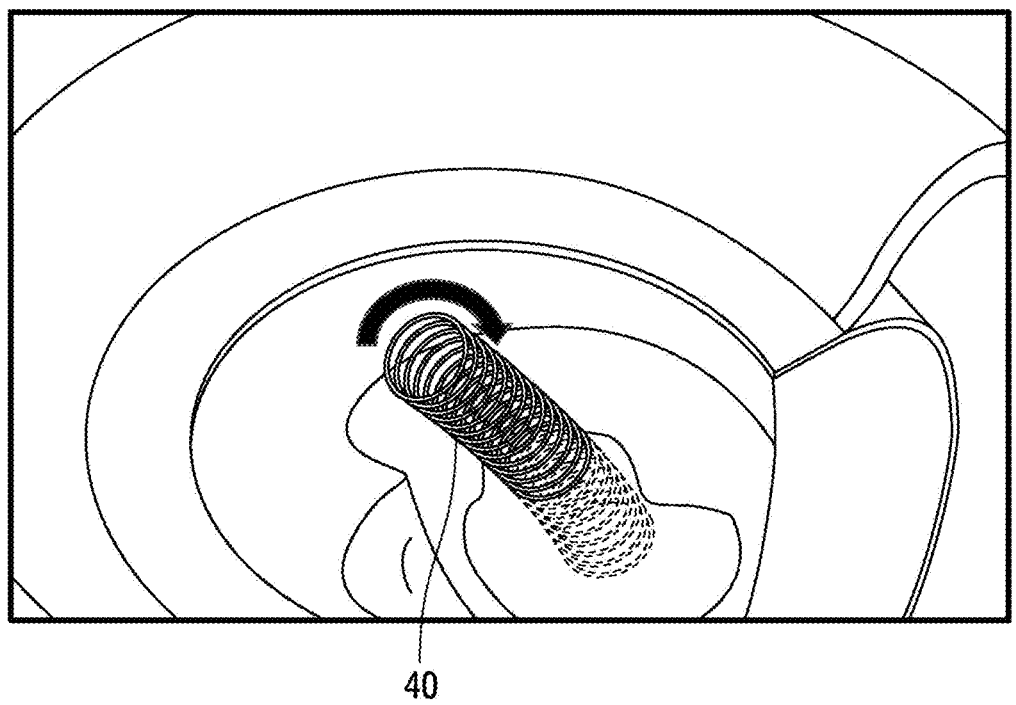
FIG. 5 shows the presently disclosed ophthalmic surgical instrument a novel method of grasping a cataract.

As FIG. 5 shows, the present disclosure provides ophthalmic surgical instrument 40, and a novel method of grasping cataract 16 for a firm hold that permits its be chopped into smaller pieces with a second instrument 34. The same device can be used to grasp cataract 16 and pull it out of the lens capsule 20. The device can either be used separately to grasp cataract 16 without the use of phacoemulsification, or it can be fit into phacoemulsification device 18 to help increase the phacoemulsification device 18 grasping power.

Not only does ophthalmic surgical instrument 40 of the present disclosure provide a novel method of grasping a cataract, it also enables grasping cataract 16 without producing any of the heat that phacoemulsification can cause. Eliminating this heat eliminates the risk of corneal wound burn. With the presently disclosed ophthalmic surgical instrument 40 there is minimal disruption of the lens capsule 20 anterior chamber. This arises because no fluid needs to flow through the eye when surgical instrument 40 is being used.

When using ophthalmic surgical instrument 40, a viscoelastic medium may be placed on to the anterior chamber and the instrument may be safely inserted into the eye through a small incision made with a keratome or sharp blade like device. This allows the anterior chamber to be very stable when using ophthalmic surgical instrument 40. Ophthalmic surgical instrument 40 may impale both soft and hard cataracts 16 equally well.

Phacoemulsification also often grasps the nucleus of hard cataracts 16 only with much difficulty after much energy has been utilized. The controlled insertion of ophthalmic surgical instrument 40 into the center of the nucleus also reduces the risk of damage to the interior lens capsule 20 by eliminating this stress.

Ophthalmic surgical instrument 40 may be approximately 3 mm wide with 1 mm between coils. However, its size may be adjusted so as to better fit through a small incision in lens capsule 20. Device 40 is intended to be inserted into the main incision during cataract surgery. The sharp end of the ophthalmic surgical instrument enters the incision first to impale the cataract. The ophthalmic surgical instrument is then twisted to create a firm grasp of the cataract.

Instead of pressing directly onto cataract 16, ophthalmic surgical instrument 40 may be controlled to rotate or pivot along the helical axis into cataract 16. The single helical coil acts much like a corkscrew being twisted on to cataract. Each 360° turn of the instrument impales the cataract one additional millimeter, when the coil pitch is 1 mm. This control is extremely important because impalement beyond the cataract would lead to a breakage of lens capsule 20 behind the lens 12.

Figure 6:
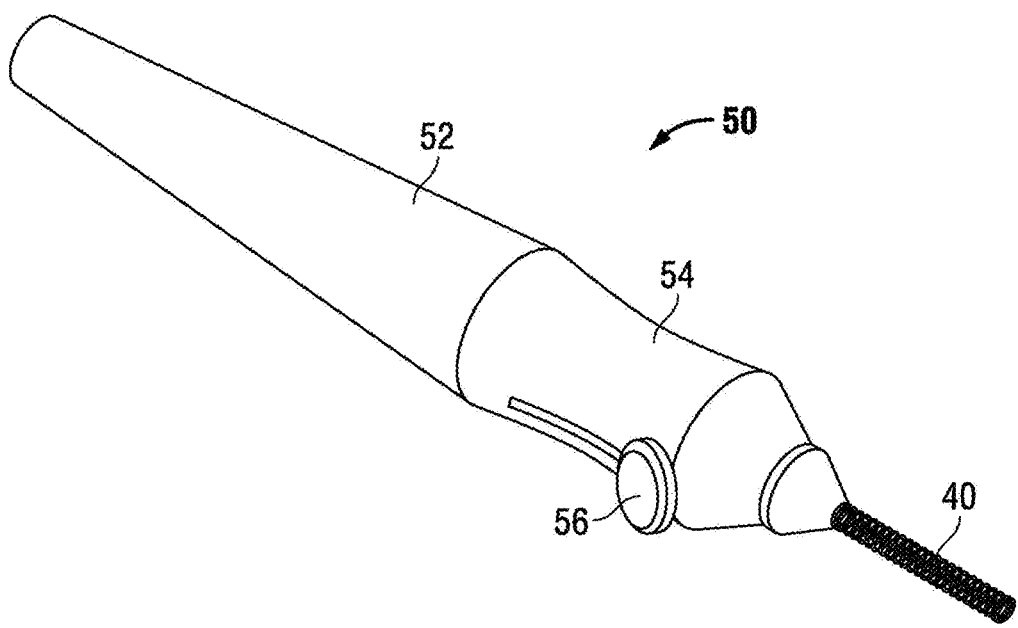
FIG. 6 provides an exemplary tool that may provide an electrically enhanced ophthalmological surgery device.

FIG. 6 provides an exemplary tool that may provide an electrically enhanced ophthalmological surgery device 50 for using surgical instrument 40 of the present disclosure. Handle component 52 includes an actuator 54 comprised of a knob 56 that can slide relative to handle component. Knob 56 serves as an actuator that controls relative and/or sliding movement between the ophthalmic surgical instrument 40 and device 50. For example, ophthalmic surgical instrument 40 can be fixed relative to the handle component 52. The applier is extended outwardly relative to the advancing member. Movement of knob 56, such as in the proximal direction, causes the applier to slide proximally into the advancing element.

Figure 7A:
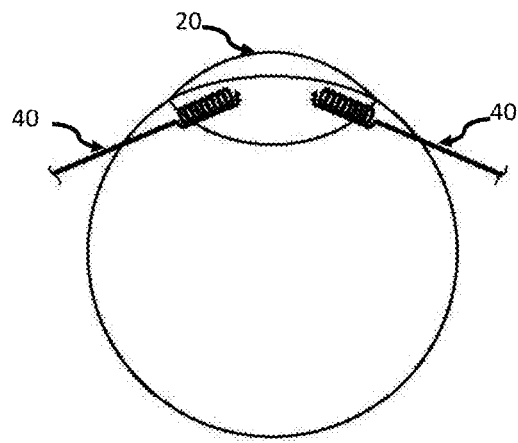
FIGS. 7A through 7C illustrate a potential use of the presently disclosed ophthalmic surgical instrument.
Figure 7B:
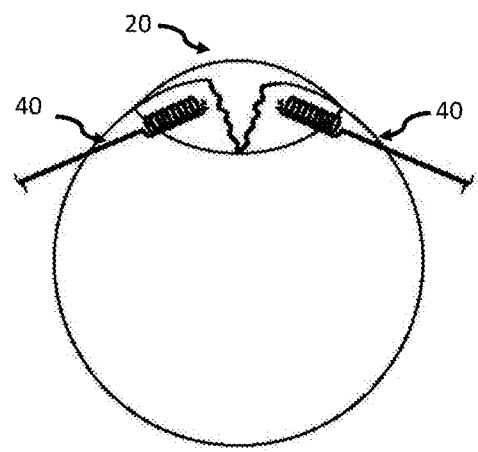
Figure 7C:
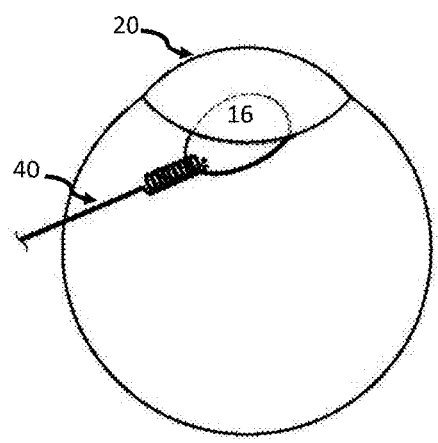

FIGS. 7A through 7C illustrate potential uses of ophthalmic surgical instrument 40. FIGS. 7A through 7B illustrate a potential use ophthalmic surgical instrument 40 for breaking open lens capsule 20 to allow access to the cataractous lens. FIG. 7C illustrates the further use of opthalmic surgical instrument 40 for impaling and removing from lens capsule 20 the cataractous lens 16. In FIG. 6, ophthalmic surgical instrument 60 is shown assisting in removing the whole lens in extra capsular cataract extraction in an extra capsular cataract extraction a large wound is made and the whole cataract is removed through the wound. Getting cataract 16 to come out of the wound can be challenging. The helical instrument can grab the cataracts easily and pull it out of The ocular capsule.

The disclosure of the present invention employs ophthalmic surgical instrument 40 that provides a precise surgical instrument for impaling cataract 16 and grasping cataract 16 at controllable depths. The control of the grasping or impalement of cataract 16 is attributable to the pitch of ophthalmic surgical instrument 40. In particular, the number of turns made into the cataract after the initial edge of the ophthalmic surgical instrument impales or sets into the cataract.

Ophthalmic surgical instrument 40 makes possible a significantly more controlled entry into the capsular bag for the surgery and prevents scraping or heating or other adverse effects associated with the slippage of other instruments seeking to grasp the cataract. Once cataract 16 has been grasped by impalement, its withdrawal from the capsular bag is easy.

Following extraction, the cataract lens will be discarded. Ophthalmic surgical instrument 40 can fit through main lens capsule 20 incision during cataract surgery to impale lens 12. Each 360° turn of surgical instrument 40 passes the device's helical wire deeper into cataract 16 for one pitch distance. Number of turns times the number of pitch equals the depth into the lens, so that with several coils into cataract 16, it is not possible for cataract 16 to slip or cause excessive friction and heat within lens capsule 20.

Figure 8:
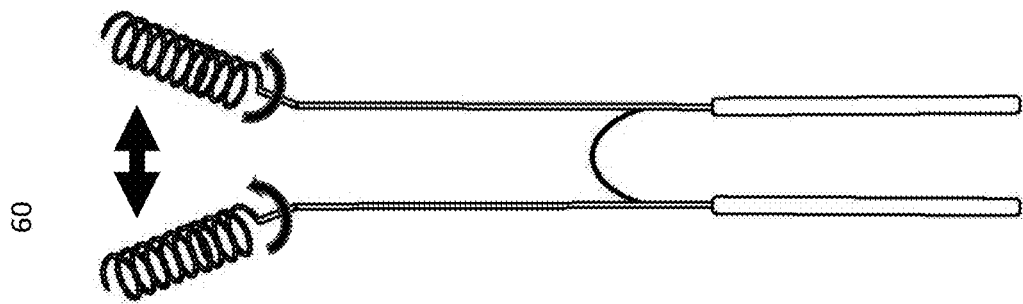
FIG. 8 shows a device utilizing two helical coils which can be rotated into a cataract.
Figure 8:
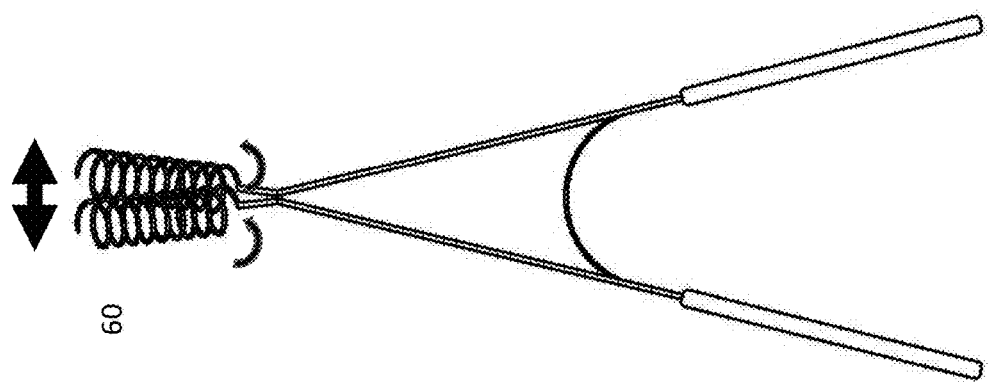
Figure 8:
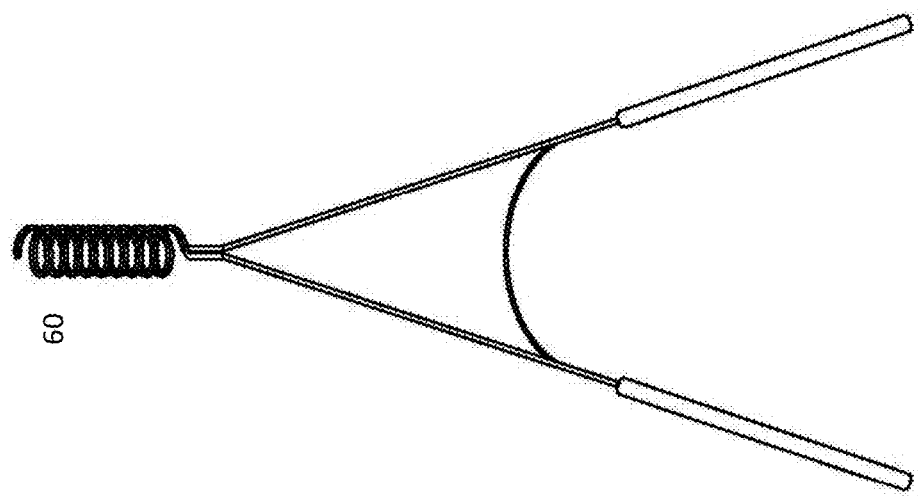

FIG. 8 shows a ophthalmic surgical forceps 60 utilizing two helical coils 61 and 63 which can be rotated into a cataractous lens 16. Squeezing the handle will separate the helical coils and this will crack the cataract into two equal pieces.

Figure 9A:
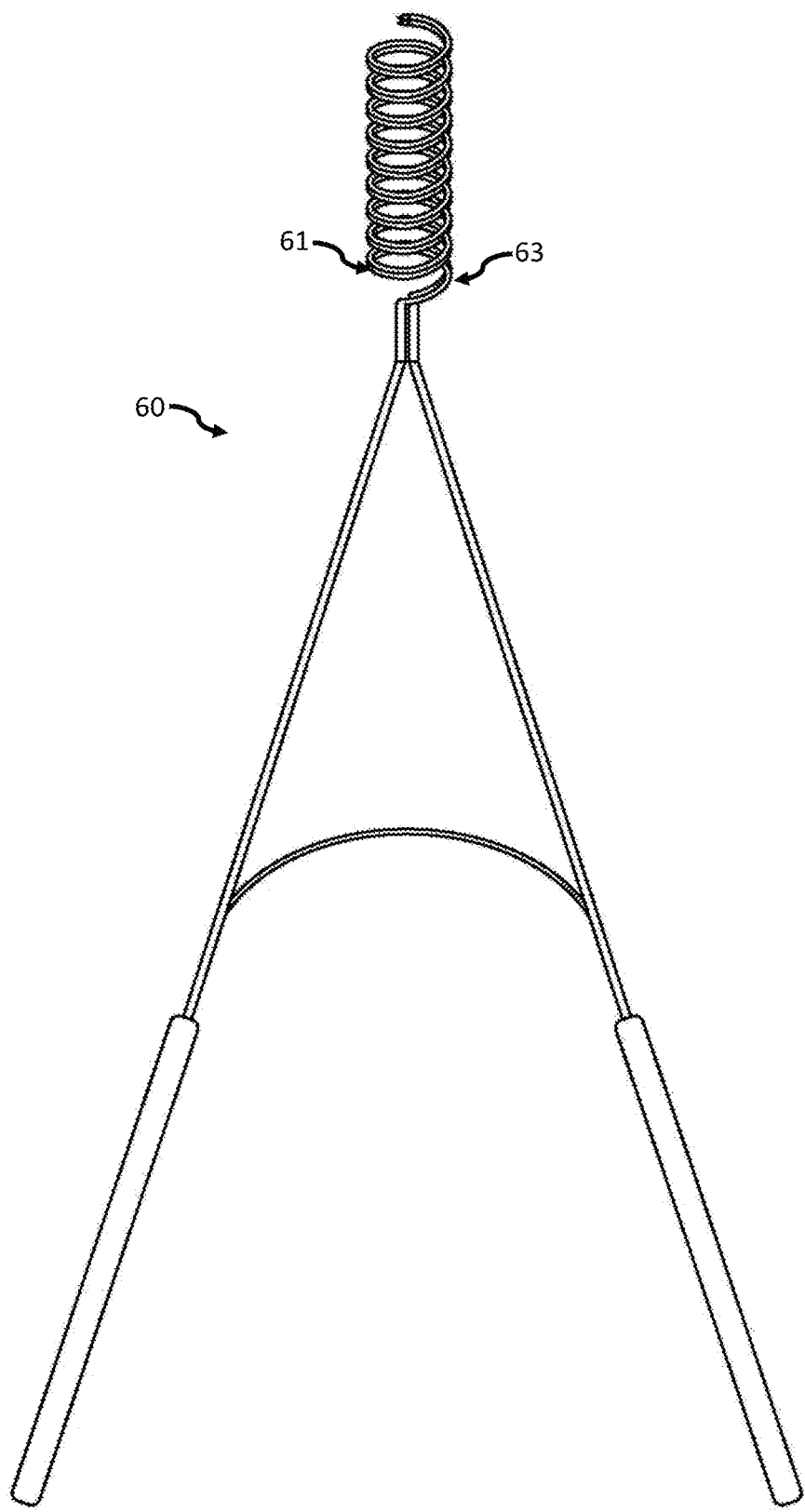
FIG. 9A shows an instrument in the closed position which can be used to impale a cataractous lens.
Figure 9B:
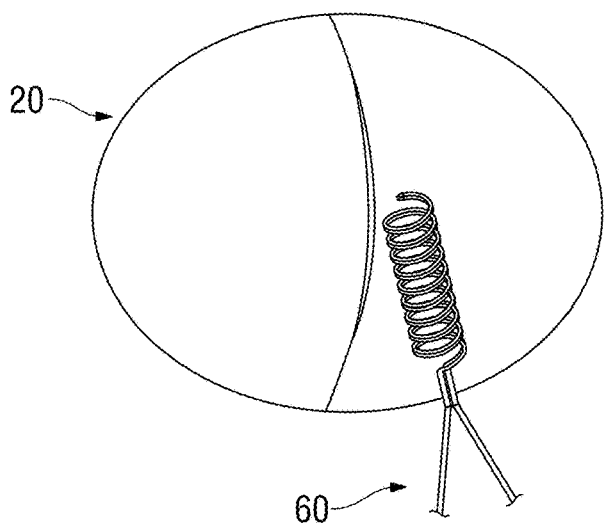
FIG. 9B shows overlapping coils can be twisted into the lens.
Figure 10B:
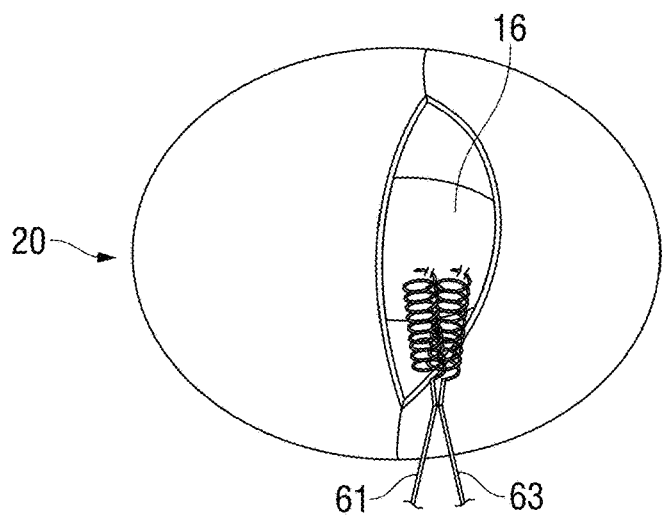
FIG. 10B shows how separating these helical coils in the substance of the cataract will crack the cataract into two pieces.
Figure 11B:
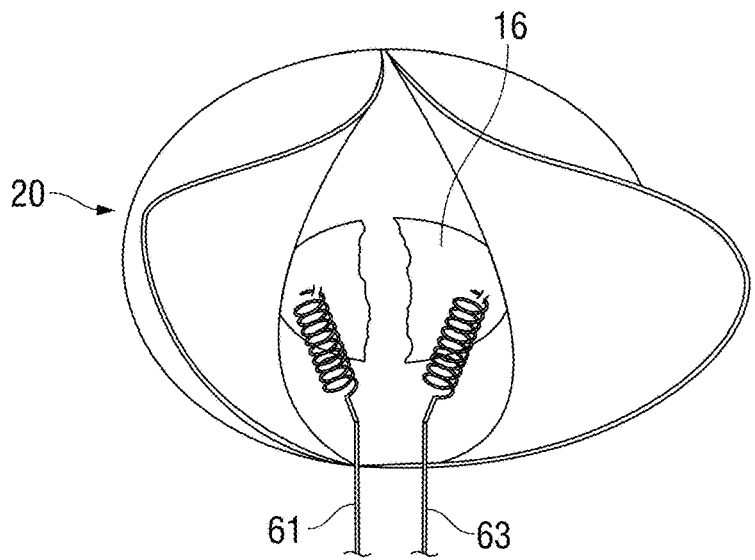
FIG. 11B The surgeon can separate the cataract halves maximally so the two pieces separate fully.
Figure 10A:
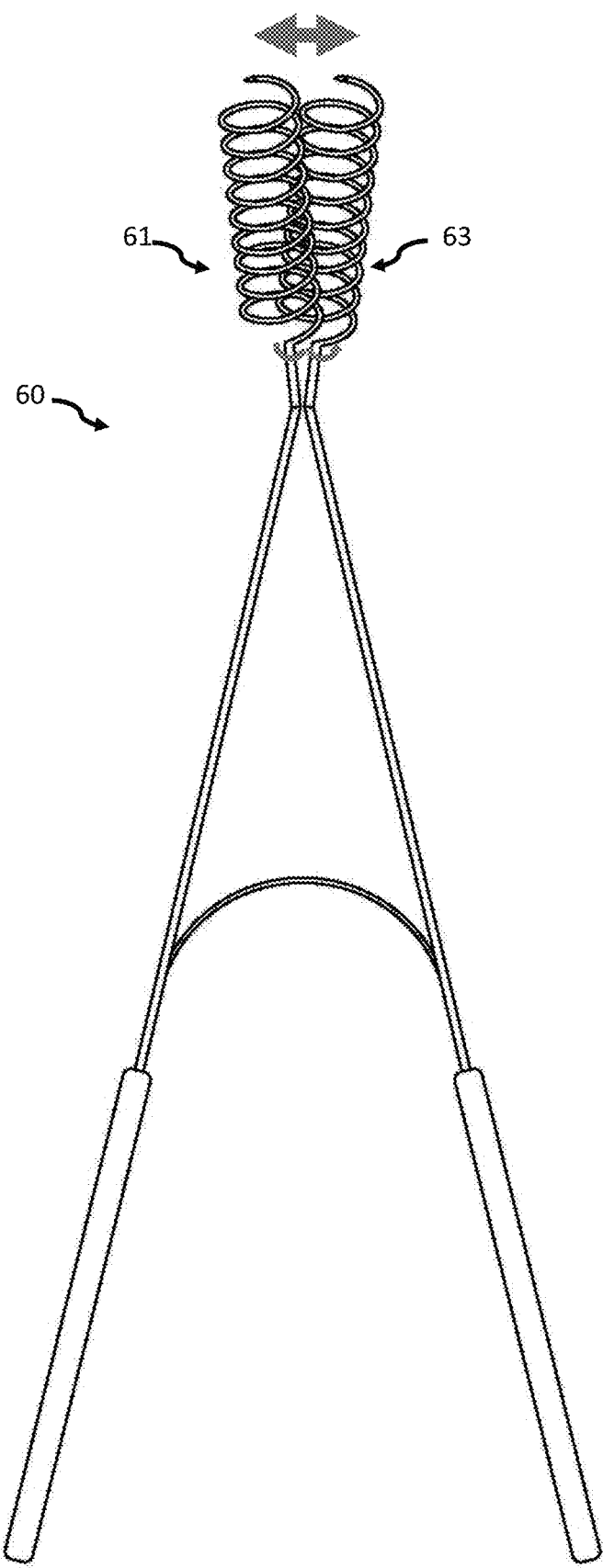
FIG. 10A shows how pressing on the handle separates the two helical coils.
Figure 11A:
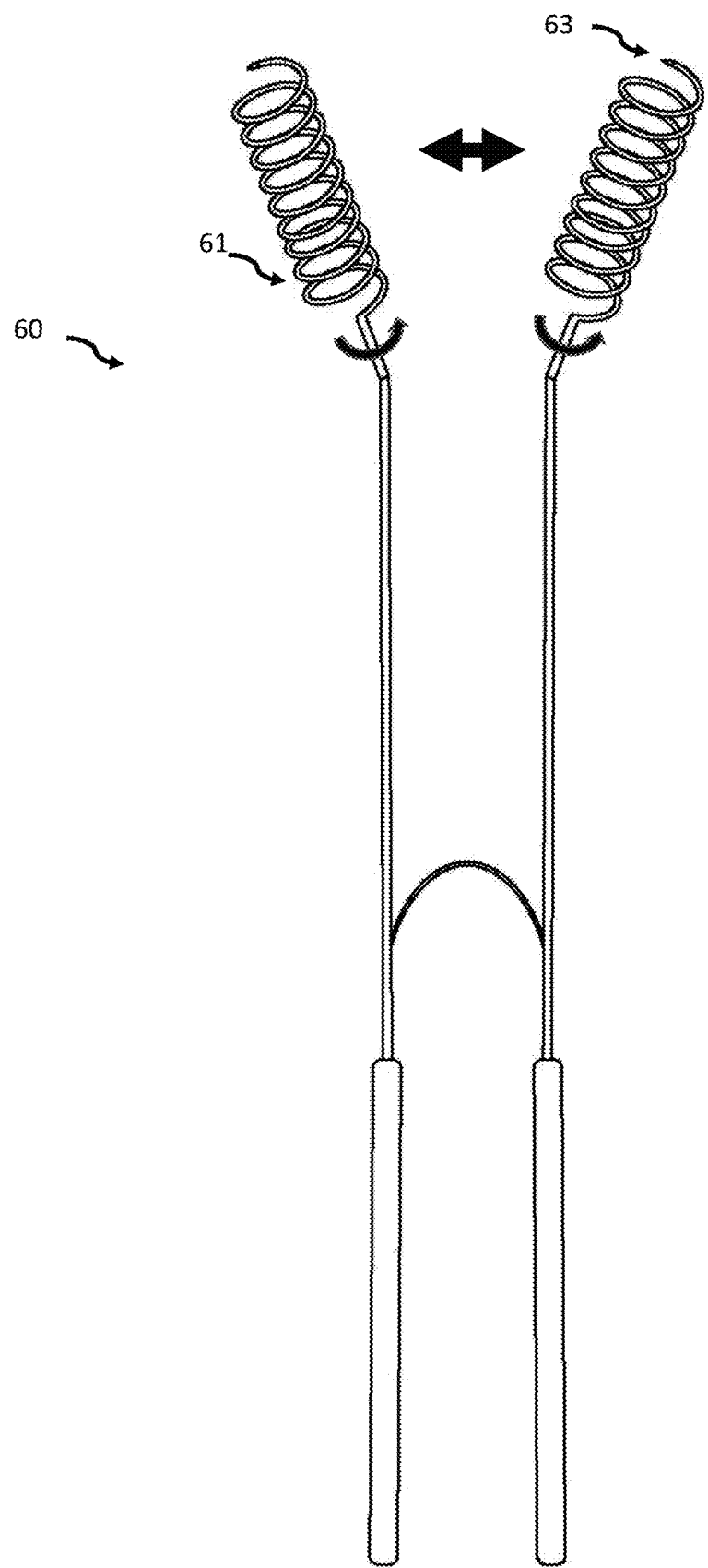
FIG. 11A shows fully separated helical coils produced by pressing the handles together.

FIG. 9A shows ophthalmic surgical forceps 60 in the closed position with helical coils 61 and 63, which can be used to impale a cataractous lens. The overlapping and juxtaposed coils 61 and 63 of ophthalmic surgical forceps 60 may be twisted into the lens as is shown in FIG. 9B. FIG. 10A shows how pressing on the handle of ophthalmic surgical forceps 60 separates the two helical coils 61 and 63. FIG. 10B shows how separating these helical coils in the substance of the cataract will crack the cataract into 2 pieces. FIGS. 11A and 11B show fully separated helical coils 61 and 63 produced by pressing the handles together. The surgeon can separate the cataract halves maximally so the two pieces separate fully. The amount of separation can be increased until the two parts of the cataract separate completely.

Figure 12:
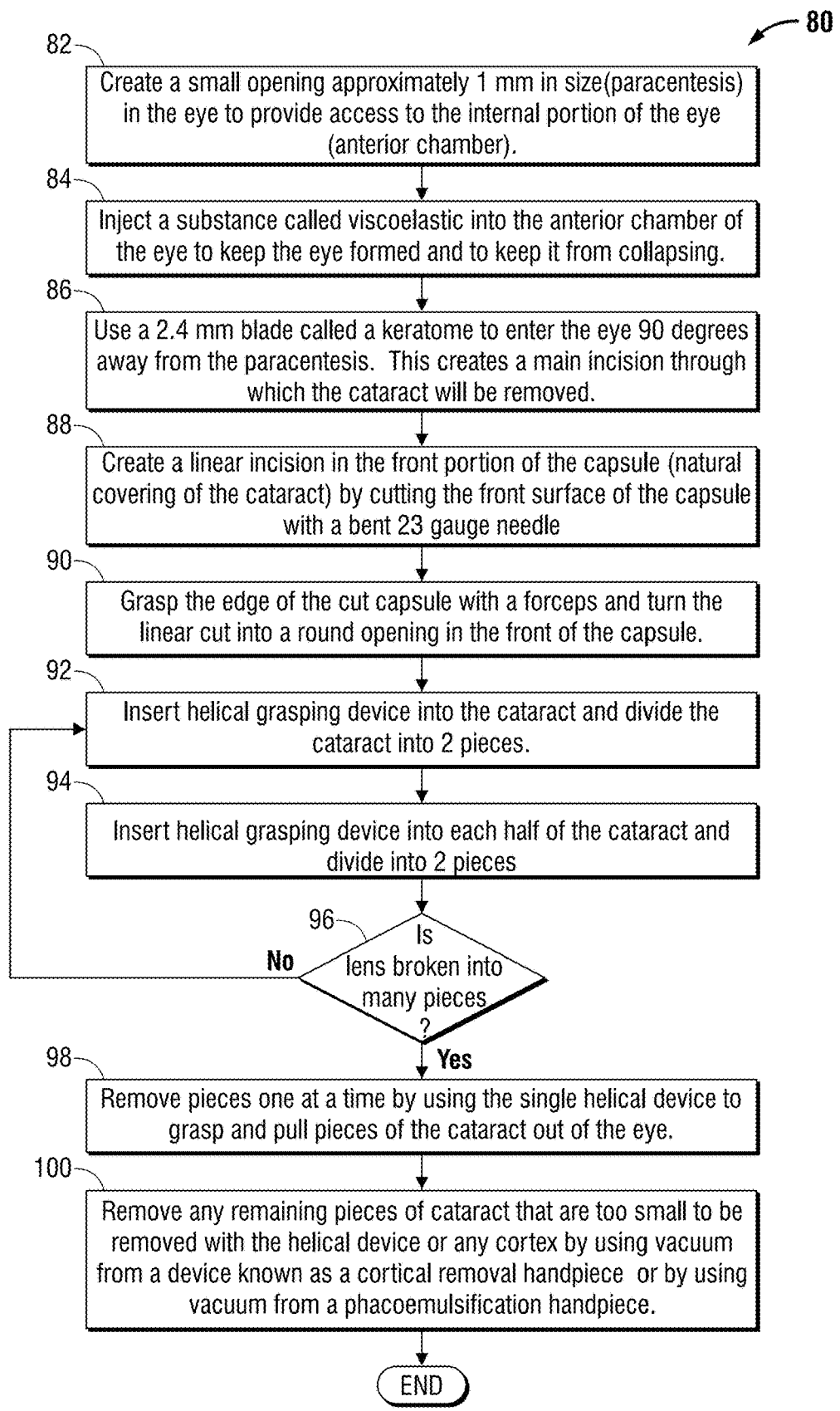
FIG. 12 provides an exemplary process for using the ophthalmic surgical instrument of the present disclosure.

FIG. 12 provides an exemplary process 80 for using the subject matter of the present disclosure. How to use ophthalmic surgical instrument. At step 82, create a small opening approximately 1 mm in size (paracentesis) in the eye to provide access to the internal portion of the eye (anterior chamber). At step 84, the ophthalologist may inject a substance called viscoelastic into the anterior chamber of the eye to keep the eye formed and to keep it from collapsing. At step 86, use a 2.4 mm blade called a keratome to enter the eye 90-degrees away from the paracentesis. This creates a main incision through which the cataract will be removed. At step 88, create a linear incision in the front portion of the capsule (natural covering of the cataract) by cutting the front surface of the capsule with a bent 23 gauge needle. At step 90, the surgeon grasps the edge of the cut capsule with a forceps and turn the linear cut into a round opening in the front of the capsule. At step 92, insert ophthalmic surgical instrument into the cataract and divide the cataract into two pieces. At step 94, he inserts ophthalmic surgical instrument 60 into each half of the cataract and divide into two pieces. At step 96, the surgeon may repeat the steps until lens is broken into many pieces. At step 98, the surgeon removes pieces one at a time by using the single helical device to grasp and pull pieces of the cataract out of the eye. At step 100, the ophthalmologist concludesd the procedure by removing any remaining pieces of cataract that are too small to be removed with the helical device or any cortex by using vacuum from a device known as a cortical removal handpiece or by using vacuum from a phacoemulsification handpiece.

In summary, the present disclosure provides a method, apparatus and system for using a new ophthalmic surgical instrument to assist in cataract removal surgery. The present disclosure includes a helical coil structure including a wire or elongated structure coiled in a plurality of turns of essentially similar diameter coils of 360-degree turns. The helical coil structure has a coil diameter sufficiently small to fit within an incision of a human ocular lens capsule for entering the human ocular lens capsule during a cataract removal surgery. A pointed sharp end of the helical coil structure for piercing and grasping a human ocular lens within the ocular lens capsule during a cataract removal surgery for controlling the position and movement of the human ocular lens. A helical coil structure handling mechanism controls the position and movement of the helical coil structure during a cataract removal surgery and while the pointed sharp end engages the cataract.

The helical coil structure handling mechanism is capable of rotating the helical coil structure during the cataract surgery for causing the pointed sharp end to pierce progressively and controllably for more or less deeply engaging the human ocular lens during the cataract removal surgery according to the needs of the surgeon performing the cataract removal surgery.

The ophthalmic surgical instrument of the present disclosure includes a helical coil structure having a pitch distance of less than approximately one millimeter for permitting rotation of the ophthalmic surgical instrument for more firmly engaging the human ocular lens without damaging tissue on the side of the human ocular lens opposite the side wherein the pointed sharp end pierces the human ocular lens. The ophthalmic surgical instrument includes a pointed sharp end of the helical coil structure for grasping the human ocular lens without producing heat during the cataract removal surgery for avoiding corneal endothelium heat damage during a cataract removal surgery. The ophthalmic surgical instrument further includes a connection with a phacoemulsification device for performing phacoemulsification of the cataract to break the cataract into smaller pieces, thereby facilitating removal of a cataract from a human ocular lens capsule.

In addition, the ophthalmic surgical instrument of present disclosure further includes a viscoelastic medium for placing into the ocular anterior chamber for stabilizing the ophthalmic surgical instrument during a cataract removal surgery for safely inserting said ophthalmic surgical instrument into the eye through a small incision in the ocular lens capsule formed by a keratome or blade-like sharp device.

The detailed description set forth herein in connection with the appended drawings is intended as a description of exemplary embodiments in which the presently disclosed subject matter may be practiced. The term "exemplary" used throughout this description means "serving as an example, instance, or illustration," and should not necessarily be construed as preferred or advantageous over other embodiments.

This detailed description of illustrative embodiments includes specific details for providing a thorough understanding of the presently disclosed subject matter. However, it will be apparent to those skilled in the art that the presently disclosed subject matter may be practiced without these specific details. In some instances, well-known structures and devices are shown in block diagram form in order to avoid obscuring the concepts of the presently disclosed method and system.

The foregoing description of embodiments is provided to enable any person skilled in the art to make and use the subject matter. Various modifications to these embodiments will be readily apparent to those skilled in the art, and the novel principles and subject matter disclosed herein may be applied to other embodiments without the use of the innovative faculty. The claimed subject matter set forth in the claims is not intended to be limited to the embodiments shown herein, but is to be accorded the widest scope consistent with the principles and novel features disclosed herein. It is contemplated that additional embodiments are within the spirit and true scope of the disclosed subject matter.

Although the ophthalmic surgical instrument for cataract removal and methods of use here disclosed have been described in detail herein with reference to the illustrative embodiments, it should be understood that the description is by way of example only and is not to be construed in a limiting sense. It is to be further understood, therefore, that numerous changes in the details of the embodiments of this disclosed process and additional embodiments of this method and system will be apparent to, and may be made by, persons of ordinary skill in the art having reference to this description. It is contemplated that all such changes and additional embodiments are within the spirit and true scope of this disclosed method and system as claimed below.

The foregoing description of embodiments is provided to enable any person skilled in the art to make and use the subject matter. Various modifications to these embodiments will be readily apparent to those skilled in the art, and the novel principles and subject matter disclosed herein may be applied to other embodiments without the use of the innovative faculty. The claimed subject matter set forth in the claims is not intended to be limited to the embodiments shown herein but is to be accorded the widest scope consistent with the principles and novel features disclosed herein. It is contemplated that additional embodiments are within the spirit and true scope of the disclosed subject matter.

What is claimed is:

1. An ophthalmic surgical instrument for assisting in cataract removal surgery, said ophthalmic surgical instrument comprising:
   a first handle and a second handle, wherein said first handle comprises a first helical coil structure at one end, wherein said second handle comprises a second helical coil structure at one end, wherein said first helical coil structure and said second helical coil structure are provided in an overlapping and juxtaposed configuration in that said first helical coil structure, said second helical coil structure, said first handle and said second handle form a shape similar to surgical forceps; wherein each free or distal end of said first helical coil structure and said second helical coil structure comprising a pointed sharp end, wherein distal ends of said first helical coil structure and said second helical coil structure are configured to be positioned over cataract lens in said overlapping and juxtaposed configuration, and wherein said first handle and said second handle are configured to be rotated for piercing said first helical coil structure and said second helical coil structure progressively and controllably into said cataract lens and grasping said cataract during a cataract removal surgery, wherein said first handle and said second handle are configured to be pressed to separate said first helical coil structure and said second helical coil structure resulting in breaking or separating said cataract lens into two or more pieces for assisting in cataract removal surgery, and wherein said first helical coil structure and said second helical coil structure comprise a pitch distance of less than approximately one millimeter, whereby each rotation of said first helical coil structure and said second helical coil structure is configured to penetrate less than approximately one millimeter deeper into said cataract lens.

2. The ophthalmic surgical instrument of claim 1, wherein said respective pointed sharp end of said first helical coil structure and said second helical coil structure are configured to grasp and hold firmly and steadily the cataract lens within the human ocular lens capsule during the cataract surgery for reducing human ocular lens movement of said cataract lens within the human ocular lens capsule, for preventing said cataract lens from producing heat during the cataract removal surgery.

3. The ophthalmic surgical instrument of claim 1, wherein said respective sharp pointed end of said first helical coil structure and said second helical coil structure are configured to grasp the cataract lens for permitting a phacoemulsification cutting device to cut the cataract lens for performing phacoemulsification of a cataract to break the cataract lens into two or more pieces, thereby facilitating removal of said cataract lens from a human ocular lens capsule.

4. The ophthalmic surgical instrument of claim 1, wherein said first handle and said second handle are connected via a connector.

* * * * *